United States Patent [19]

Frangie

[11] Patent Number: 5,510,891
[45] Date of Patent: Apr. 23, 1996

[54] OBJECT CHARACTERISTIC DIRECT MEASURING DEVICE UTILIZING A MAGNETICALLY ATTRACTED LOVER BASE AND AN UPPER FRAME HAVING A SCALED LENS THEREIN

[76] Inventor: Nehme Frangie, 125 Wolf Rd., #313, Albany, N.Y. 12205

[21] Appl. No.: 376,788

[22] Filed: Jan. 23, 1995

[51] Int. Cl.⁶ .............................. G01N 21/00; G02B 27/02
[52] U.S. Cl. ............................ 356/30; 356/397; 359/801; 359/804; 292/251.5
[58] Field of Search ..................... 356/30, 397; 73/104; 63/32; 359/436, 442, 801, 804; 206/6.1, 305, 1.5, 477, 486–490; 292/251.5

[56] References Cited

U.S. PATENT DOCUMENTS

| | | | |
|---|---|---|---|
| 1,001,991 | 8/1911 | Sale | 356/30 |
| 1,700,496 | 1/1929 | Heitzler | 356/30 |
| 3,398,631 | 8/1968 | McGivern et al. | 356/397 |
| 3,398,639 | 8/1968 | Dakin | 356/397 |
| 3,451,706 | 6/1969 | Baermann | 292/251.5 |
| 3,539,264 | 11/1970 | Moore et al. | 356/397 |
| 3,610,756 | 10/1971 | Lenzen et al. | 356/30 |
| 3,749,301 | 7/1973 | Peckar | 292/251.5 |
| 3,765,775 | 10/1973 | Ganssle et al. | |
| 3,822,906 | 7/1974 | Gaines | 292/251.5 |
| 4,265,476 | 5/1981 | Elgart | 294/64 R |
| 4,460,211 | 7/1984 | Pomeroy | 294/99 R |
| 4,508,449 | 4/1985 | Okazaki | 356/30 |
| 4,906,083 | 3/1990 | Sattler | |
| 5,064,281 | 11/1991 | Davis | 356/30 |
| 5,196,966 | 3/1993 | Yamashita | 359/804 |
| 5,260,763 | 11/1993 | Yamashita | 359/804 |
| 5,306,467 | 4/1994 | Douglas-Hamilton et al. | 422/99 |

FOREIGN PATENT DOCUMENTS 5-269661  10/1993  Japan.

*Primary Examiner*—Frank Gonzalez
*Assistant Examiner*—Jason D. Eisenberg
*Attorney, Agent, or Firm*—John R. Flanagan

[57] ABSTRACT

An object characteristic direct measuring device includes a lower base, a first annular magnetic element disposed in the lower base, and a holder member surrounded by the first magnetic element and being mounted by the lower base and adapted to receive and hold an object, such as a gem. The measuring device further includes an upper frame having a central aperture receiving an upper portion of the holder member, a transparent lens disposed across the top of the central aperture in the upper frame, a graduated measuring scale applied on the transparent lens for use in measuring a dimension of the gem held by the holder member mounted to the lower base, and a second annular magnetic element disposed in a bottom groove in the upper frame which surrounds the central aperture therein and magnetically attracts the first magnetic element in the lower base so as to retain the upper frame upon the lower base while permitting rotation of the upper frame relative to the lower base and holder member for alignment of the measuring scale with the desired dimension of the gem.

21 Claims, 1 Drawing Sheet

OBJECT CHARACTERISTIC DIRECT MEASURING DEVICE UTILIZING A MAGNETICALLY ATTRACTED LOVER BASE AND AN UPPER FRAME HAVING A SCALED LENS THEREIN

BACKGROUND OF THE INVENTION

1. Field of the Invention

The present invention generally relates to measuring the dimensions of objects such as precious stones and, more particularly, is concerned with a device for precisely and directly measuring a characteristic of an object such as the table facet of a diamond.

2. Description of the Prior Art

Gems such as diamonds have for centuries been viewed as prized possessions. The value of a gem is affected by many factors, including its color, cut, clarity and carat weight. In order to appraise its value, it is necessary for gem dealers and consumers to closely examine a gem. The narrow edge of a gem at its widest part is commonly referred to as the gem girdle. The gem pavilion is the portion below the girdle and the gem crown is the portion above the girdle. A table facet is found in the form of a flat surface on the crown. The table is the largest facet on a cut gem.

The table percentage of the girdle diameter is one of the important factors considered in the valuation of a gem. The longest table measurement is divided by the average girdle diameter to determine what is referred to as the table percentage. Gem dealers and consumers look to this percentage as a way to place value on a gem.

A problem exists, however, in accurately measuring the table facet of a gem. Up until now, the most common method for measuring gems has been holding a transparent millimeter ruler in one hand over a gem held by tweezers in the other hand. The dexterity required, however, to hold a gem by tweezers or some other manual stone holder while measuring the table facet, is too great for many people who find that their hands shake too much to permit the proper alignment of the gem and measuring device.

Devices have been developed over the years for the examination of precious stones. Representative examples are disclosed in U.S. Pat. No. 1,001,991 to Sale, U.S. Pat. No. 1,700,496 to Heitzler, U.S. Pat. No. 3,610,756 to Lenzen et al., U.S. Pat. No. 3,765,775 to Ganssle et al., U.S. Pat. No. 4,265,476 to Elgart, U.S. Pat. No. 4,460,211 to Pomeroy, U.S. Pat. No. 4,508,449 to Okazaki, U.S. Pat. No. 4,906,083 to Sattler, U.S. Pat. No. 5,064,281 to Davis and U.S. Pat. No. 5,306,467 to Douglas-Hamilton et al. Many of these devices, however, are for identification or for determining the color or optical density of a stone, and are not specifically adaptable to taking measurements of the table facets of gems.

Consequently, a need still exists for a device that directly enables the user to accurately measure the table facet and other areas of a gem in order to determine the value of the stone.

SUMMARY OF THE INVENTION

The present invention provides a device for direct measuring of a characteristic of an object, particularly of a gem, being designed to satisfy the aforementioned need. The principal advantage of the present invention is that it enables the user to measure the table facet and other areas of a gem without having to hold the gem by tweezers and the measuring scale by hand, eliminating the above mentioned dexterity problem.

Accordingly, the present invention is directed to a object characteristic direct measuring device. The measuring device comprises: (a) a lower base, (b) an upper frame supported upon the lower base and having a central aperture extending through the upper frame; (c) means for holding an object to be measured, the holding means being mounted to the lower base and extending upwardly therefrom into the central aperture of the upper frame; (d) a transparent lens disposed on the upper frame across the central aperture therein and above the holding means; (e) a graduated measuring scale applied on the transparent lens for use in measuring a characteristic of the object held by the holding means; and (f) means for producing a magnetic attraction between the lower base and upper frame being sufficient to retain the upper frame upon the lower base while permitting rotation of the upper frame relative to the lower base and holding means mounted thereto for alignment of the measuring scale with the characteristic of the object to be measured. The magnetic attraction producing means includes a first magnetic element disposed in the lower base and a second magnetic element disposed in the upper frame and surrounding the central aperture therein and magnetically attracting the first magnetic element in the lower base.

More particularly, the lower base has a cylindrical interior cavity being open at a bottom of the lower base and closed at a top thereof except for a top central opening therethrough. The first magnet element is annular, has a central bore and is disposed in the interior cavity of the lower base. The central bore of the first magnetic element is aligned with the top central opening of the lower base. The holding means is preferably a cylindrical plug of compressible foam material disposed through the central bore of the first annular magnetic element and extending upwardly through the top central opening of the lower base and into the central aperture of the upper frame. The foam plug has a slit therein open at the top of the plug for receiving and holding the object therein. A skid resistant pad is attached to the bottom of the lower base and closes the bottom of the interior cavity thereof along the bottom of the lower base.

The central aperture of the upper frame extends between the top and bottom thereof and receives an upper portion of the plug upwardly through the central aperture from the bottom of the upper frame. The upper frame also has an annular top recessed ledge which surrounds a top end of the central aperture. The transparent lens is disposed in the central aperture and seated upon the annular top recessed ledge. The second annular magnetic element is disposed in an annular bottom groove defined in the bottom of the upper frame and surrounding the central aperture of the upper frame.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Figure 1:
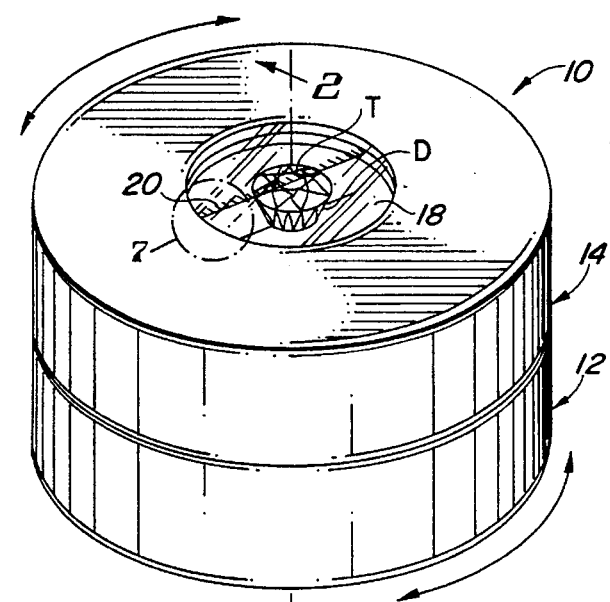
FIG. 1 is a perspective view of an object characteristic direct measuring device of the present invention.
Figure 2:
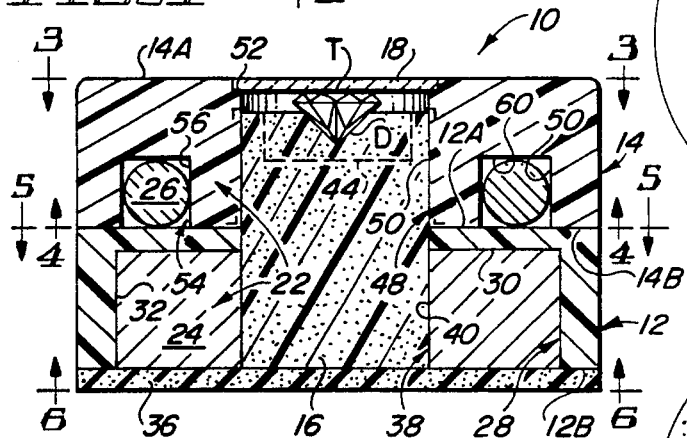
FIG. 2 is a cross-sectional view of the measuring device taken along line 2—2 of FIG. 1.
Figure 5:
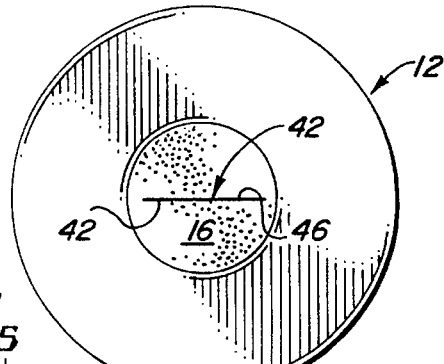
FIG. 5 is a reduced top plan view of a lower base of the measuring device as seen along line 5—5 of FIG. 2.

Referring to the drawings and particularly to FIGS. 1 and 2, there is illustrated an object characteristic direct measuring device, generally designated 10, of the present invention. The measuring device 10 can be used to measure a selected characteristic of an object, such as a dimension, and particularly is adapted to enable a user to measure a table facet T of a diamond D as well as to measure various areas of gems in general, without creating a dexterity problem. Thus, while the measuring device 10 is particularly suited for measuring gems, it is not so limited in its applications.

The measuring device 10 basically includes a lower base 12, an upper frame 14 supported upon the lower base 12, an object holder member 16 mounted to the lower base 12 and having an upper portion 16A disposed in the upper frame 14 and receiving and holding an object, such as the diamond D, a transparent lens 18 with a graduated measuring scale 20 thereon supported on the upper frame 14, and magnetic means 22 for producing a magnetic attraction between the lower base 12 and upper frame 14. The attractive force of the magnetic field produced is sufficient to retain the upper frame 14 supported upon and in general alignment with the lower base 12. The magnetic force is also sufficient to prevent unintended relative movement between the lower base 12 and upper frame 14 while, at the same time, permitting rotation of the upper frame 14 relative to the lower base 12 and holder member 16 for aligning the graduated measuring scale 20 with the characteristic of the object to be measured, such as the table facet T of the diamond D. Once the graduated measuring scale 20 has been placed into alignment with the table facet T of the gem D and the rotation of the upper frame 14 stopped, the magnetic attractive force will retain the upper frame 14 at that desired position on the lower base 12 while the scale 20 is read.

Preferably, the magnetic attraction producing means 22 of the measuring device 10 takes the form of a first magnetic element 24 disposed in the lower base 12 and a second magnetic element 26 disposed in the upper frame 14. Preferably, the first and second magnetic elements 24, 26 are separate components from the lower base 12 and upper frame 14 with the latter being made of suitable non-ferrous material. Alternatively, it is within the purview of the present invention that the lower base 12 and upper frame 14 can be provided as permanent magnets themselves with the first and second magnetic elements 24, 26 integral parts thereof.

Referring to FIGS. 1, 2, 5 and 6, the lower base 12 of the measuring device 10 is a body preferably of a cylindrical shape but which can be of other shapes. The body of the lower base 12 has an interior cavity 28 defined by a planar interior top wall 30 spaced below a top 12A of the lower base 12 and a cylindrical interior side wall 32 which extends between the interior top wall 30 and a bottom 12B of the lower base 12. Thus, the interior cavity 28 is open from the bottom 12A of the lower base 12 and closed across the top 12B of the lower base 12, except for a top central opening 34 defined therethrough. Also, a skid resistant pad 36, preferably circular in shape, is attached to the bottom 12B of the lower base 12 and thereby covers and closes the interior cavity 28 thereof along the bottom 12B of the lower base 12 and assists in maintaining the lower base 12 stationary as the upper frame 14 is rotated relative thereto when the device 10 is in use.

Figure 6:
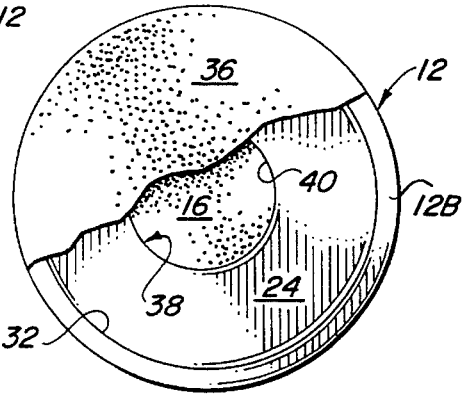
FIG. 6 is a reduced bottom plan view of the lower base of the measuring device as seen along line 6—6 of FIG. 2, with a portion of a bottom skid resistant pad being broken away.
Figure 3:
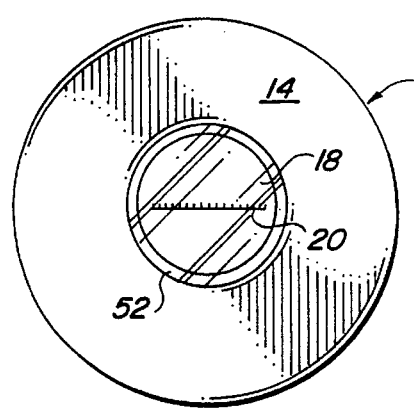
FIG. 3 is a reduced top plan view of an upper frame of the measuring device as seen along line 3—3 of FIG. 2.

Referring to FIGS. 2 and 6, the first magnetic element 24 of the measuring device 10, which is preferably annular in shape, has a central bore 38 defined by a cylindrical internal wall 40 in the first magnetic element 24. The first magnetic element 24 resides in the interior cavity 28 of the lower base 12 and is retained therein in any suitable manner, such as by the application of an adhesive and/or by the presence of the pad 36 attached on the bottom 12B of the lower base 12. The central bore 38 of the first magnetic element 24 is aligned with the top central opening 34 of the lower base 12.

Referring to FIGS. 2–6, the object holder member 16 is preferably a cylindrical body or plug 16 disposed through the central bore 38 of the first annular magnetic element 24 with the upper portion 16A of the plug extending upwardly through the top central opening 34 of the lower base 12. Preferably, the plug 16 is made of a compressible foam material, although it can also be made from other suitable materials. The plug 16 has a slit 42 therein extending short of the full diameter of the plug 16 and defined by an interior bottom surface 44 and a pair of interior facing surfaces 46. The slit 42 is open at a top 16B of the plug 16 for receiving and holding the object therein to be measured, such as the diamond D as shown in FIGS. 1 and 2. Thus, the first magnetic element 24 and holder member or plug 16 fill the entire volume of the interior cavity 38 with the first magnetic element 24 filling a larger proportion thereof.

Referring to FIGS. 1–4, the upper frame 14 of the measuring device 10 is a body also preferably of a cylindrical shape but which can be of other shapes. The body of the upper frame 14 has a central aperture 48 defined by a cylindrical interior side surface 50 extending between and opening at the top 14A and bottom 14B thereof. The upper frame 14 receives the upper portion 16A of the plug 16 extending upwardly through the central aperture 48 from the bottom 14B of the upper frame 14. The upper frame 14 also has an annular top recessed ledge 52 which surrounds a top end 48A of the central aperture 48.

Figure 4:
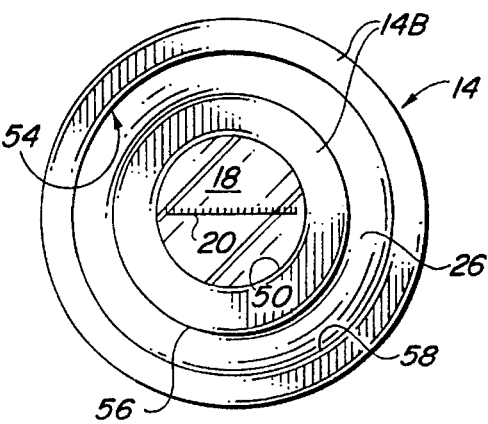
FIG. 4 is a reduced bottom plan view of the upper frame of the measuring device as seen along line 4—4 of FIG. 2.
Figure 7:
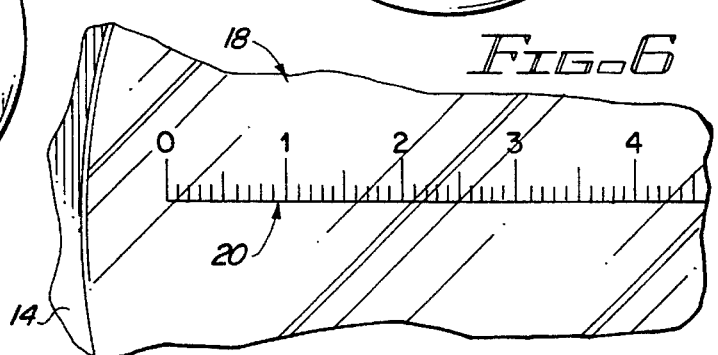
FIG. 7 is an enlarged detailed view of a portion of a transparent lens and graduated measuring scale of the measuring device encompassed by circle 7 of FIG. 1.

As seen in FIGS. 1, 4 and 7, the transparent lens 18 of the measuring device 10 is preferably planar and circular in shape and composed of a suitable material, such as glass or plastic. The transparent lens 18 is removably disposed in the top 48A of the central aperture 48 and seated upon the annular top recessed ledge 52 of the upper frame 14 and overlies the object D held on the top of the plug 16. The graduated measuring scale 20 is applied across the transparent lens 22 and has a length generally equal to the diameter of the central aperture 48 or at least to the length of the slit 42 in the plug 16. The measuring scale 20 can take many different forms, depending upon the particular measurement being carried out. The transparent lens 18 is preferably removable so that one transparent lens can be interchanged for another having a different scale thereon.

Referring to FIGS. 2 and 4, the second magnetic element 26 is annular in shape and is disposed in an annular bottom groove 54 defined in the bottom 14B of the upper frame 14 and surrounding the central aperture 48 therethrough. The annular bottom groove 54 is defined by a pair of radically spaced inner and outer facing walls 56, 58 and an upper wall 60 extending between them. The second magnetic element 26 can be adhesively secured within the annular groove 54. As seen in its preferred embodiment in FIG. 4, second magnetic element 26 is continuous. Alternatively, second magnetic element 26 can be in sections (not shown).

While the measuring device 10 has been described and illustrated herein as a stand-alone device, it may be incorporated as part of an apparatus which includes lighting and/or magnification components. Also, while the first and second elements 24, 26 are characterized as "magnetic" elements, only one of them needs to be made of a material that constitutes a permanent magnet. The other element can made of a ferromagnetic material which is magnetically attracted to the one permanent magnet. Alternatively, both elements 24, 26 can be permanent magnets. The term "magnetic" is used to cover all of these alternatives.

While the present invention will be understood from the foregoing description, it will be apparent that various changes may be made thereto without departing from the spirit and scope of the invention, the form hereinbefore described being merely a preferred or exemplary embodiment thereof.

I claim:

1. An object characteristic direct measuring device, comprising:

(a) a lower base;

(b) an upper frame disposed upon said lower base and having a central aperture extending through said upper frame;

(c) means for holding an object to be measured, said holding means being mounted to said lower base and extending upwardly therefrom into said central aperture of said upper frame;

(d) a transparent lens disposed on said upper frame across said central aperture therein and above said holding means; and (e) a graduated measuring scale applied on said transparent lens for use in measuring a characteristic of the object held by said holding means;

(f) said upper frame being rotatable about and relative to said holding means extending into said central aperture of said upper frame and relative to said lower base for moving said measuring scale relative to said holding means and to thereby align said measuring scale with a characteristic of the object to be measured.

2. The device of claim 1 further comprising:

(g) means for producing a magnetic attraction between said lower base and upper frame being sufficient to retain said upper frame upon said lower base while permitting said rotation of said upper frame relative to said lower base.

3. The device of claim 2 wherein said magnetic attraction producing means includes a first magnetic element disposed in said lower base.

4. The device of claim 3 wherein said magnetic attraction producing means further includes a second magnetic element disposed in said upper frame surrounding said central aperture and magnetically attracting said first magnetic element in said lower base.

5. The device of claim 3 wherein:

said upper frame has an annular bottom groove defined in a bottom of said upper frame and surrounding said central aperture thereof; and said magnetic attraction producing means includes a second magnetic element disposed in said annular bottom groove of said upper frame and extending about said central aperture therein.

6. The device of claim 2 wherein:

said lower base has an interior cavity open at a bottom of said lower base and closed at a top thereof except for a top central opening defined therethrough; and said magnetic attraction producing means includes a first magnetic element disposed in said interior cavity of said lower base, said first magnetic element being annular in shape and having a central bore aligned with said top central opening of said lower base and central aperture of said upper frame, said holding means being a plug of foam material stationarily mounted in said central bore of said first magnetic element and extending upwardly therefrom through said top central opening of said lower base and into said central aperture of said upper frame.

7. The device of claim 2 wherein:

said lower base has an interior cavity and top central opening; and said magnetic attraction producing means includes a first magnetic element disposed in said interior cavity of said lower base.

8. The device of claim 7 further comprising:

a skid resistant pad attached to a bottom of said lower base and covering and closing said interior cavity along said bottom of said lower base.

9. The device of claim 1 further comprising:

a skid resistant pad attached to a bottom of said lower base.

10. The device of claim 1 wherein said holding means is a plug of foam material having a slit therein being open at a top of said plug for receiving and holding the object therein.

11. The device of claim 1 wherein said central aperture of said upper frame extends between a top and a bottom of said upper frame and receives an upper portion of said holding means therein extending upwardly through said central aperture from said bottom of said upper frame.

12. The device of claim 1 wherein said upper frame has an annular top recessed ledge defined in a top of said upper frame and surrounding a top end of said central aperture.

13. The device of claim 10 wherein said transparent lens is disposed in said top of said central aperture and seated upon said annular top recessed ledge.

14. An object characteristic direct measuring device, comprising:

(a) a lower base having an interior cavity and top central opening;

(b) an upper frame disposed upon said lower base and having a central aperture extending through said upper frame and an annular bottom groove defined in a bottom of said upper frame and surrounding said central aperture thereof;

(c) means for holding an object to be measured, said holding means being mounted to said lower base and extending upwardly therefrom into said central aperture of said upper frame;

(d) a transparent lens disposed on said upper frame across said central aperture therein and above said holding means;

(e) a graduated measuring scale applied on said transparent lens for use in measuring a characteristic of the object held by said holding means; and (f) means for producing a magnetic attraction between said lower base and upper frame being sufficient to retain said upper frame upon said lower base while permitting rotation of said upper frame relative to said lower base and said holding means mounted thereto for alignment of said measuring scale with a characteristic of the object to be measured, said magnetic attraction producing means includes
  (i) a first magnetic element disposed in said interior cavity of said lower base, said first magnetic element being annular in shape and having a central bore aligned with said top central opening of said lower base and central aperture of said upper frame,
  (ii) a second magnetic element disposed in said annular bottom groove of said upper frame and extending about said central aperture therein and magnetically attracting said first magnetic element in said lower base.

15. The device of claim 14 wherein said holding means is a plug of material being stationarily mounted in said central bore of said first magnetic element and extending upwardly therefrom through said top central opening of said lower base and into said central aperture of said upper frame.

16. The device of claim 15 wherein said plug of material has a slit therein being open at a top of said plug for receiving and holding the object therein.

17. The device of claim 15 wherein said material of said plug is a compressible foam material.

18. The device of claim 14 further comprising:
  a skid resistant pad attached to a bottom of said lower base and covering and closing said interior cavity along said bottom of said lower base.

19. The device of claim 14 wherein said central aperture of said upper frame extends between a top and a bottom of said upper frame and receives an upper portion of said holding means therein extending upwardly through said central aperture from said bottom of said upper frame.

20. The device of claim 14 wherein said upper frame has an annular top recessed ledge defined in a top of said upper frame and surrounding a top end of said central aperture.

21. The device of claim 20 wherein said transparent lens is disposed in said top of said central aperture and seated upon said annular top recessed ledge.

\* \* \* \* \*